(12) United States Patent
Granegger

(10) Patent No.: US 12,251,549 B2
(45) Date of Patent: *Mar. 18, 2025

(54) ROTARY BLOOD PUMP FOR REGULATING A HEMODYNAMIC PARAMETER SUCCESSIVELY TO DIFFERENT TARGET VALUES

(71) Applicant: Berlin Heart GmbH, Berlin (AT)

(72) Inventor: Marcus Granegger, Perchtoldsdorf (AT)

(73) Assignee: Berlin Heart GmbH, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/356,807

(22) Filed: Jul. 21, 2023

(65) Prior Publication Data

US 2023/0355957 A1 Nov. 9, 2023

Related U.S. Application Data

(63) Continuation of application No. 17/091,632, filed on Nov. 6, 2020, now Pat. No. 11,724,096, which is a
(Continued)

(30) Foreign Application Priority Data

Dec. 14, 2015 (EP) ..................... 15199776

(51) Int. Cl.
*A61M 60/554* (2021.01)
*A61M 60/148* (2021.01)
(Continued)

(52) U.S. Cl.
CPC ........ *A61M 60/422* (2021.01); *A61M 60/148* (2021.01); *A61M 60/178* (2021.01);
(Continued)

(58) Field of Classification Search
None
See application file for complete search history.

(56) References Cited

U.S. PATENT DOCUMENTS 6,974,436 B1 12/2005 Aboul-Hosn et al.
9,352,077 B2 5/2016 Arndt et al.
(Continued)

FOREIGN PATENT DOCUMENTS

CN 101815547 A 8/2010
CN 102365104 A 2/2012
(Continued)

OTHER PUBLICATIONS

English translation of International Search Report, issued in International Application No. PCT/EP2016/076391, dated Jan. 30, 2017, pp. 1-2, European Patent Office, Rijswijk, The Netherlands.
(Continued)

*Primary Examiner* — Kennedy Schaetzle
(74) *Attorney, Agent, or Firm* — Crowell & Moring LLP

(57) ABSTRACT

A blood pump for supporting the heart may be provided that includes: a rotor with delivery elements; a rotor drive; a pressure sensor; and a regulating device that regulates a pressure or a hemodynamic parameter by means of control of the rotor drive. The pressure and/or the hemodynamic parameter may be determined by means of one or a plurality of hemodynamic sensors and/or from operating parameters of the pump. The regulating device may be suitable for regulating a hemodynamic parameter successively, such as periodically, to different target values. Using such regulation, the blood pump may be operated in an optimized manner, and operation of the blood pump may be varied in a targeted and patient-protective manner in order to attain certain goals.

19 Claims, 2 Drawing Sheets

Related U.S. Application Data continuation of application No. 16/060,487, filed as application No. PCT/EP2016/076391 on Nov. 2, 2016, now Pat. No. 10,857,275.

(51) Int. Cl.
*A61M 60/178* (2021.01)
*A61M 60/216* (2021.01)
*A61M 60/422* (2021.01)
*A61M 60/515* (2021.01)
*A61M 60/531* (2021.01)

(52) U.S. Cl.
CPC ........ *A61M 60/216* (2021.01); *A61M 60/515* (2021.01); *A61M 60/531* (2021.01); *A61M 60/554* (2021.01); *A61M 2205/3303* (2013.01); *A61M 2205/3334* (2013.01); *A61M 2205/50* (2013.01); *A61M 2230/06* (2013.01); *A61M 2230/30* (2013.01)

(56) References Cited

U.S. PATENT DOCUMENTS

| | | | |
|---|---|---|---|
| 10,857,275 B2 * | 12/2020 | Granegger | A61M 60/554 |
| 11,724,096 B2 * | 8/2023 | Granegger | A61M 60/515 600/17 |
| 2003/0045772 A1 | 3/2003 | Reich et al. | |
| 2006/0069299 A1 | 3/2006 | Aboul-Hosn | |
| 2010/0222633 A1 | 9/2010 | Poirier | |
| 2012/0078030 A1 * | 3/2012 | Bourque | A61M 60/178 600/16 |
| 2013/0267764 A1 | 10/2013 | Poirier | |
| 2015/0246166 A1 * | 9/2015 | Greatrex | A61M 60/178 600/17 |

FOREIGN PATENT DOCUMENTS

| | | |
|---|---|---|
| CN | 104043153 A | 9/2014 |
| CN | 104822400 A | 8/2015 |

OTHER PUBLICATIONS

First Notification of Office Action with English translation, issued in CN application 2016800726788, dated Aug. 3, 2020, pp. 1-25, China National Intellectual Property Administration, Beijing, CN.

* cited by examiner

ROTARY BLOOD PUMP FOR REGULATING A HEMODYNAMIC PARAMETER SUCCESSIVELY TO DIFFERENT TARGET VALUES

CROSS-REFERENCE TO RELATED APPLICATIONS

This is a Continuation of U.S. application Ser. No. 17/091,632 filed Nov. 6, 2020, which is a Continuation of U.S. application Ser. No. 16/060,487 filed Jun. 8, 2018, now U.S. Pat. No. 10,857,275 issued Dec. 8, 2020, which is a 371 nationalization of international patent application PCT/EP2016/076391 filed Nov. 2, 2016, which claims priority under 35 USC § 119 to European patent application 15 199 776.4 filed Dec. 14, 2015. The entire contents of each of the above-identified applications are hereby incorporated by reference.

TECHNICAL FIELD

The invention is in the field of mechanical and electrical engineering, and may be used particularly advantageously in medical engineering.

DETAILED DESCRIPTION

Figure 1:
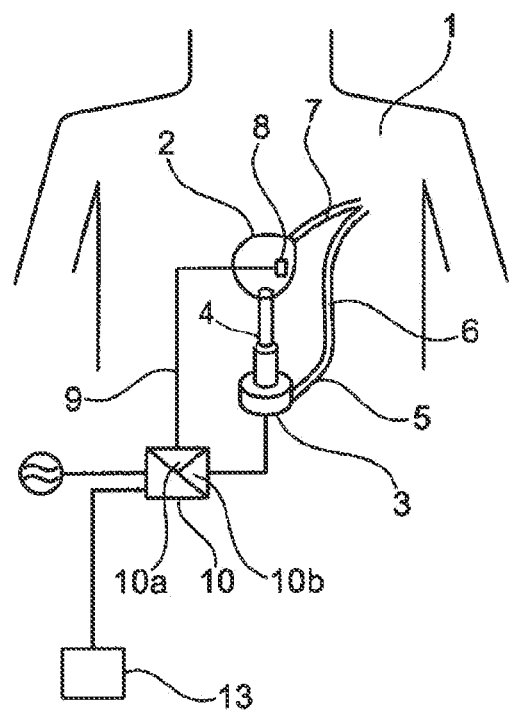
FIG. 1 is a schematic depiction of a heart pump device having a regulating device.

Specifically, the invention relates to blood pumps as are used for supporting the heart in human patients. Such pumps are employed to support the delivery of blood from a right or left ventricle. Such pumps may be implanted for this purpose or may be provided externally on the patient's body, wherein in either case at least one cannula projects into a chamber of the heart.

Such pumps are often embodied as rotary pumps having a pump rotor that supports delivery elements that transport the blood to be delivered in the rotor's radial or axial direction. Such rotary pumps have the advantage that pump parameters, such as, for example, flow rate or a pressure built up via the pump, may be controlled or regulated via a speed of the pump. It is also possible to easily vary such parameters by controlling or regulating the speed. Varying the speed by means of the control, for example, may change the blood flow such that the pump, heart ventricle, or other regions of the blood flow are washed out so that the formation of thrombi may be prevented. In addition, changing the speed may control the performance of the pump such that the aortic valve may be intentionally opened using the remaining heart function and the pressure that builds as a result thereof.

In principle, the measure of the speed variations required for these effects is not known for an individual patient, so that during operation it is not possible to ensure that the desired consequence of a variation in speed will occur.

Given the background of the prior art, the underlying object of the present innovation is to create a blood pump and a method for its operation with which it is possible to reliably adjust certain hemodynamic parameters using variations in speed. Another object is to make more complex measurements possible when certain hemodynamic parameters have been attained.

The present innovation thus relates to a blood pump for supporting the heart, having a rotor with delivery elements and having a rotor drive and having a pressure sensor or another hemodynamic sensor and a regulating device, which, by means of actuating the rotor drive, regulates a pressure or a hemodynamic parameter, wherein in particular the pressure and/or the hemodynamic parameter are determined by means of one or more hemodynamic sensors and/or from operating parameters of the pump.

By means of the pressure sensor, a pressure that occurs for example in a ventricle or at a different location through which blood flows may be measured directly at specific times in the heart rhythm, or a pressure curve as a function of time. Since it is possible to periodically record, by means of the pressure sensor in conjunction with a processing device and in particular with a memory device, the exact pressure curve in a ventricle or at a different location through which the blood flows, it is also possible to determine other hemodynamic parameters from the periodic pressure curve, such as for example, the end-diastolic pressure in a ventricle, pressure pulsality, increase or drop in pressure dP/dt, or even the maximum of the increase or decrease in pressure. In this way it is possible to determine, for example, an estimate of contractility as a ratio (slope) in the curve, in which various measured values of the end-diastolic pressure are related to the measured maximum dP/dtmax of the pressure curve. The end-diastolic pressure (EDP) may be varied by changing the speed of the pump, the change in the end-diastolic pressure may be tracked, and the dP/dtmax values during these variations may be measured. The slope of this curve is a contractility index that is independent of preload or afterload.

In order to be able to conduct such measurements well, the innovation may be embodied such that successively different parameter values, in particular alternating periodically, may be prespecified or are prespecifiable as target value to the regulating device for the pressure or a hemodynamic parameter. Thus, in the example given above, successively different values of the end-diastolic pressure may be set by regulating the speed of the pump and the values for dP/dtmax may be determined. This may also occur periodically.

The end-diastolic pressure is determined from the cyclical pressure curve in the detection region of the pressure sensor, and the speed of the pump is regulated in a regulation process such that the end-diastolic pressure is adjusted to successively different target values. This regulation sequence may be repeated periodically. A regulating device within the system that also contains the blood pump is correspondingly suitable for detecting or determining the desired hemodynamic pressure parameters, and, where necessary, basing further regulation of the pump speed on the deviation from a target value, and thus adjusting the target value.

In addition, it may be provided that a detection device for detecting the change in pressure per unit of time in the detection region of the pressure sensor and for determining the maximum and/or minimum of this value in a heart cycle is provided. The detection of the change in the pressure per unit of time may occur using a running measurement of the pressure and by determining changes in pressure in specific periods of time by means of a processing device. The value for the dP/dt and its maximum and/or minimum is thus detected or determined over the course of a heart cycle.

In addition, a processing device may be provided that relates the determined maximum values of the pressure changes to the adjusted target pressure parameters, in particular to the end-diastolic pressure regulated or detected as target value, especially determines a quotient from the determined maximum values of the pressure change and the adjusted target pressure parameters (end-diastolic fill pressure values). This quotient provides a contractility index that is independent of the degree of support and of the preload and afterload of the ventricle in question.

It may also be provided that the processing device is suitable for determining the slope of a line that is provided by the linear relationship between the determined maximum values of the changes in pressure and the adjusted target pressure parameters, in particular the end-diastolic pressure.

In addition, for realizing the innovation it may also be provided that the processing device determines a quotient from a difference of two or more maximum values in the changes in pressure and the target pressure parameters associated with these values, especially the end-diastolic pressure.

Alternatively or in addition it may also be provided that an echocardiograph is provided for conducting echocardiographic measurements and is triggered by or synchronized with the changes in the control of the rotor drive.

The echocardiograph may be positioned and set up such that it detects regions of a patient's body that come into direct contact with the flow of the blood that passes through the patient's heart, such as, for example, spaces/chambers of the heart through which blood flows, parts of the connecting blood vessels, the region of the heart valves, and even parts of a blood pump.

By coupling the echocardiography with speed variations it is possible to detect morphological parameters, such as for example the end-diastolic diameter and the end-diastolic volume of a heart chamber, and to determine their correlation with pressure parameters, at the same time the pressure curves are detected. A contractility index for the specific ventricle may also be determined from the relationship between the end-diastolic volume of the ventricle and the maximum change in pressure per unit of time dP/dtmax.

Another advantageous embodiment of the innovation may provide that the regulating device is set up to regulate the rotor drive to varying target values during operation, such that at least one prespecified feature of a temporal curve of the pressure, a flow, a motor current, or a bearing position is attained. The modes of operation of the regulating device are thus not limited to attempting to reach certain pressure values when controlling the pump, but rather a feature of a parameter curve, such as for instance the achievement of a maximum or of a certain value on the slope/first derivative or of a curve shape, may be sought as the target value for the regulation. These types of parameters are, for example, the detected ventricular pressure, a flow (flow rate or volume flow rate) of the blood flow through the pump, a motor current, the bearing position of an axial bearing of a rotor of the pump, or a variable derived from temporal curves of these parameters. During the course of the heart cycle, these parameters also experience cyclical events so that the parameter curves recur in the cycle of the heart activity. This makes it possible for the regulating device to check that the sought target value has been achieved in every cycle and to readjust the control of the pump motor if necessary.

In doing so, the target values prespecified for regulation may also be varied systematically in order to create, in a defined manner, changing conditions during operation of the blood pump. This may be implemented, for example, in that an opening of an aortic valve is verifiable due to a detected signal curve and/or a hemodynamic variable or operating parameter of the pump. The opening of the aortic valve may be verified, for example, using the pressure curve in the ventricle or using the curve of the motor load during a heart cycle.

The pump motor may be controlled, for example, in that the pump power is dropped until the preload is sufficient to permit build-up of pressure due to remaining heart activity, causing the aortic valve to open. The explanation for this is that when there is sufficient pump power, the blood is delivered out of the ventricle by the pump in a regular manner so that during intensive pump operation the preload of the ventricle may not be sufficient to generate a pressure within the ventricle that is sufficient for opening the aortic valve.

Known from the prior art is achieving opening of the aortic valve by regularly reducing the pump power. Due to the lack of regulation, however, the degree of the reduction in pump power is not adapted individually, and it may happen that the pump power is reduced more than necessary so that, although the aortic valve opens, the delivery of blood by the pump, and therefore also the perfusion of the end organs, is low in this period of time.

It may also be provided that the regulating device has a first operating state, which corresponds to a first operation of the pump, and a second operating state, which is set up to regulate the rotor drive for an interval of time such that an opening of aortic valve may be evidenced due to a detected signal curve and/or a hemodynamic variable or an operating parameter of the pump.

It may also be provided that a switch device is provided that switches between the first operating state and the second operating state according to a prespecified time pattern.

Normally, optimized support of the heart activity of the patient due to the blood pump takes place in the first operating state. This first operating state may be designed, for example, such that no aortic valve opening or no reliable, regular aortic valve opening takes place. By switching to the second operation, it is assured that an aortic valve opening actually takes place due to the changed preload, wherein this aortic valve opening is evidenced by a hemodynamic variable and/or the curve of an operating parameter of the pump. Thus it is assured that that there is an opening of the aortic valve, but the pump activity does not drop more than required.

The information obtained using such variations in speed (contractility index, opening of aortic valve) is also suitable for adjusting the heart support from the blood pump individually for the patient and, for instance, for weaning the patient from the support by the heart pump.

It may also be provided that the hemodynamic parameter that is regulated by the regulating device is the pulsality of the pressure difference along the pump or of a through-flow rate through the pump. To this end, the maxima and minima of the pressure values and through-flow rates are determined and the associated values are measured and differences found. Pressure sensors, for example, may be provided at the inlet and outlet of the pump to this end.

The innovation may also be embodied in that a pressure sensor, in particular an absolute pressure sensor or a flow sensor, is directly connected to a regulating device. The aforesaid types of sensors detect variables that are directly related to the blood flow. Thus hemodynamic parameters may be measured directly and additional hemodynamic parameters may be determined. Independently of this, different sensors or sensor devices may be provided that allow operating parameters of the pump or of the rotor to be detected, such as, for example, a current measurement sensor, voltage sensor, speed sensor, and/or a sensor that detects the axial pressure of the rotor on an axial bearing. For example, it is possible to estimate a pressure difference produced by a pump using the axial load acting on a bearing. For instance in the case of a magnetic bearing, the pressure acting on an axial bearing may be estimated by monitoring the bearing position. In the case of a regulated magnetic bearing, the bearing current required for bearing regulation may also be used to this end.

In addition, a pressure sensor device having two pressure sensors may also be provided for measuring a pressure, of which two pressure sensors a first pressure sensor is arranged in or on the pump and a second pressure sensor is arranged in a volume not directly connected to the pump, for example in the thorax outside of the patient's heart or connected to the atmosphere outside the patient's body. In this way it is possible to correct the pressure measurement in the ventricle or immediately in the pump with respect to variable external pressures, such as, for example, with respect to variable atmospheric pressure.

By taking into account measured pressures outside of the heart in the thorax of the patient, changes in pressure through the patient's respiration may be accounted for and compensated/eliminated computationally.

In addition to a blood pump of the type described above, the innovation also relates to a method for operating such a pump and in particular provides that a pressure or a hemodynamic parameter is intermittently regulated by means of a regulating device of the rotor drive, wherein in particular the pressure and/or the hemodynamic parameter is determined by means of a pressure sensor device and/or hemodynamic sensors and/or from operating parameters of the pump.

The innovation shall be illustrated using the figures and explained in the following.

Figure 2:
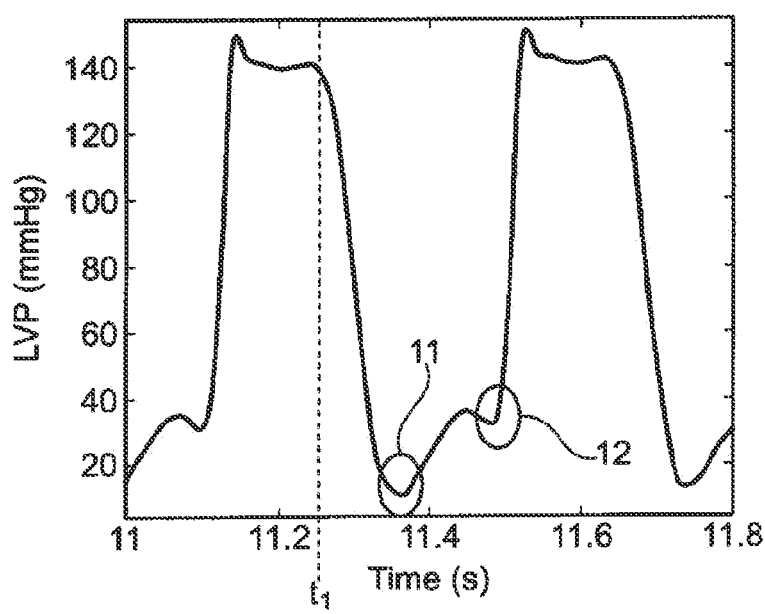
FIG. 2 is a schematic diagram of the pressure curve during a heart cycle.
Figure 3:
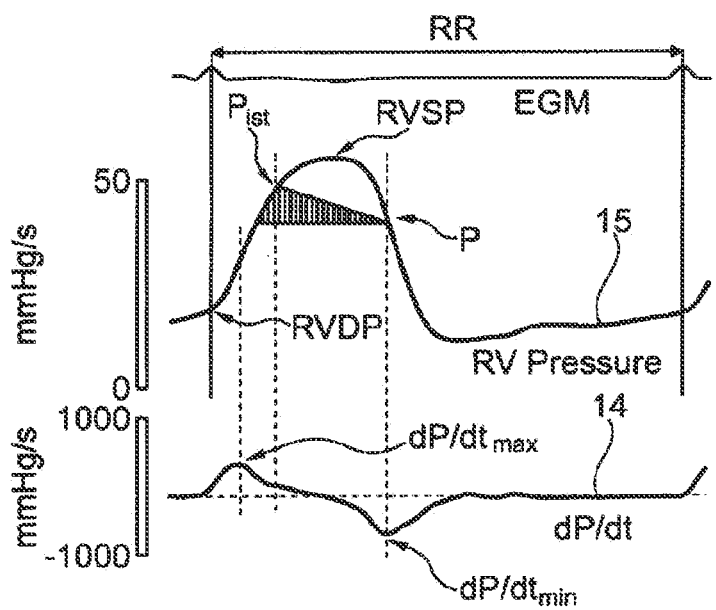
FIG. 3 provides two diagrams with the pressure curve in a heart ventricle and the temporal derivative of this variable; and, FIG. 4 is a diagram in which the end-diastolic pressure against $dP/dt_{max}$ is plotted.
Figure 4:
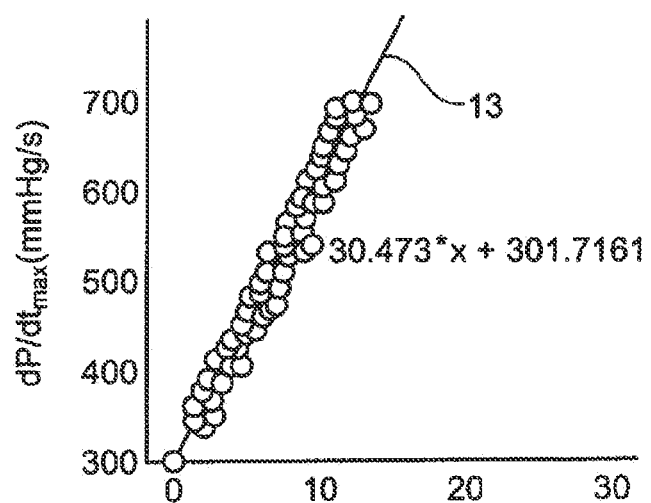

FIG. 1 is a schematic depiction of a heart pump device having a regulating device;

FIG. 2 is a schematic diagram of the pressure curve during a heart cycle;

FIG. 3 provides two diagrams with the pressure curve in a heart ventricle and the temporal derivative of this variable; and, FIG. 4 is a diagram in which the end-diastolic pressure against dP/dtmax is plotted.

FIG. 1 is a schematic depiction of the body 1 of a patient and a heart 2 to be supported and a rotary pump 3 arranged on the heart. The pump 3 is connected by means of an inlet cannula 4 to the heart 2 of the patient and draws blood out of the right ventricle in order to deliver it to the pump outlet 5 and through the outlet cannula 6 into the aorta 7. Also provided is a pressure sensor 8 that is connected via a line 9 to a regulating device 10. The latter has a memory device 10a and an analysis device 10b for analyzing hemodynamic pressure curves and for deriving or determining parameters therefrom.

Instead of an individually measured pressure or pressure curve, a pressure difference, measured by two pressure sensors, may also be determined as a measured value, for example, a pressure difference between pump inlet and pump outlet or a pressure difference between a location on the pump or in a ventricle, on the one hand, and in the thorax outside of the patient's heart, on the other hand.

Thus, a detected pressure curve may be detected and stored in the memory device 10a of the regulating device 10 over one or a plurality of heart cycles. As shall be illustrated more precisely below, different characteristic hemodynamic parameters may be determined from the pressure curve or from the curve of another detected variable, such as the pump load or the speed of the pump, or from combinations of parameters. The regulating device may be operated such that certain hemodynamic parameter values are attained. The target values for the hemodynamic parameters to be regulated may be changeable and over the course of time may be changed according to prespecified rules, for instance also recurring periodically. In this way the pump may also be operated according to a program alternately in two different operating states.

The pressure curve in the left ventricle of a heart may be schematically depicted using FIG. 2. The time in seconds is plotted on the horizontal axis, while the pressure in millimeters of mercury is plotted on the vertical axis. The observation may be initiated at time t1 shortly after 11.2 seconds when the pressure in the left ventricle drops, i.e., the ventricle relaxes. After the active relaxation phase, the ventricle filling phase begins and the ventricle pressure attains its absolute minimum, which is highlighted by the first marking circle 11. As the ventricle refills, the ventricular pressure rises slowly until the left ventricle contracts in the systole. The pressure rises sharply at the beginning of the systole in the isovolumetric contraction phase. The end-diastolic fill pressure, marked with the circle 12, is at the transition between the slow increase in the diastole and the rapid increase in the systole.

When there is a change in the physiological load of the patient, both the minimum diastolic pressure 11 and the end-diastolic fill pressure 19 change. Both aforesaid values may be determined simply from the detected pressure curve using the analysis device 10b in the regulating device after the conclusion of one or a plurality of heart cycles. If the speed of the pump is changed by the regulating device, the characteristic values, especially the end-diastolic fill pressure, may also be influenced by this.

FIG. 3 depicts two diagrams, one above the other, wherein the pressure curve 15 of a ventricle pressure for a heart cycle between the end of a first diastole and the end of a second diastole is depicted in the upper diagram. The ventricle pressure increases to a maximum and then drops at the end of the systole.

Depicted in the lower portion of the illustration in FIG. 3 is the temporal derivative dP/dt of the pressure curve depicted in the top diagram for the same period of time.

It is evident that there are two clear extremes, first, on the left side of the curve 14, the point at which the rate of change dP/dt is at its maximum (dP/dtmax). An extreme in the form of the minimum dp/dtmin of the rate of change is also attained in the region of the dropping flank, that is, the drop in pressure. In addition to the temporal position of the maximum and minimum values of the change in pressure per unit of time, the absolute values dP/dtmax and dP/dtmin are also significant.

One use of the innovation provides that the end-diastolic pressure (EDP) is intentionally varied between different values by changing the pump speed, and the value of the maximum dP/dtmax is measured during these variations. It turns out that for different values of the pump speed the end-diastolic pressures and the maximums dP/dtmax in the diagram (see FIG. 4) associated with them are on a straight line, the slope of which is constant and represents a contractility index independent of the preload and afterload.

In FIG. 4, the end-diastolic fill pressure is plotted on the horizontal axis, while the associated values dP/dtmax are plotted on the vertical axis. The various measurement points are, to a good approximation, disposed on an increasing straight line 13.

Consequently, regulation of the pump to a specific end-diastolic fill pressure at which dP/dtmax is then determined is required for the measurement. If such a measurement point is detected, regulation to a different target value of the corresponding hemodynamic parameter, specifically, the end-diastolic fill pressure, is set, and another measurement point is detected and so on.

Reliable aortic valve opening by means of regulating the pump represents another example for the use of the invention. Opening of the aortic valve may be evidenced using certain parameters of the curve of the measured left ventricular pressure or using certain changeable operating parameters of the pump, such as for example, the difference in pressure and/or a throughput in the pump, i.e., the amount delivered per time.

Under certain conditions, regular opening of the aortic valve is important. If the aortic valve does not open, i.e., opening is not detectable using analysis of the detected parameters, the pump is readjusted; for example, the pump speed is reduced until the aortic valve opens.

The advantage of this method is that the speed is reduced only until opening of the aortic valve is actually achieved. Thus it is possible to prevent the speed of the blood pump from dropping too far.

Thus it is also possible, for example, to measure contractility and other hemodynamic parameters by means of the invention when using LVADs (left ventricular assist devices) and RVADs (right ventricular assist devices) by using small, automatically regulated speed variations. This reduces risks for patients, and contractility may be controlled more frequently. In addition, it is possible to rapidly determine recovery of a supported heart in this manner, so that the odds of weaning off of heart support increase.

If the invention is used for attaining regular reliable opening of the aortic valve, this may contribute to preventing aortic valve insufficiency in LVAD patients. In addition, because of the minimized speed reduction, it may be possible to prevent short-term undersupply of blood to the patient's body.

If pulsatility is selected as a regulating parameter, it is also possible by means of the invention to reproduce the natural pulsatility of the heart by means of pump regulation. The adjusted pulsatility may also be modified periodically.

The invention claimed is:

1. A blood pump for supporting a heart, the blood pump comprising:
    a rotor with delivery elements;
    a rotor drive;
    a hemodynamic sensor;
    a regulating device configured to regulate a hemodynamic parameter by control of the rotor drive, wherein the regulating device is configured to regulate a specific hemodynamic parameter successively to different target values;
    wherein the regulating device is configured to regulate to varying target values during operation of the rotor drive such that at least one prespecified feature of a temporal curve of a pressure, a flow, a motor current, or a bearing position is attained; and
    wherein the hemodynamic parameter that is regulated by the regulating device is the pulsatility of a pressure difference along the blood pump or of a flow rate through the blood pump.

2. The blood pump according to claim 1, wherein the hemodynamic sensor is configured to determine the hemodynamic parameter, and/or the regulating device is configured to determine the hemodynamic parameter from operating parameters of the blood pump.

3. The blood pump according to claim 1, wherein the regulating device is embodied such that the hemodynamic parameter is determined by means of one or a plurality of hemodynamic sensors and/or from operating parameters of the blood pump.

4. The blood pump according to claim 1, wherein the regulating device is configured to use an end-diastolic pressure determined from a cyclic pressure curve in the detection range of the pressure sensor.

5. The blood pump according to claim 1, wherein the regulating device is suitable for periodically regulating to different target values.

6. The blood pump according to claim 1, wherein the regulating device is configured to regulate the rotor drive alternating periodically such that an opening of the aortic valve may be evidenced based on a detected signal curve and/or a hemodynamic variable or an operating parameter of the blood pump.

7. The blood pump according to claim 6, wherein an adjusted target pressure parameter is end-diastolic pressure.

8. The blood pump according to claim 6, wherein the pressure sensor is an absolute pressure sensor.

9. The blood pump according to claim 1, wherein the regulating device has a first operating state that corresponds to a first operation of the blood pump and a second operating state that is configured to regulate the rotor drive for a time interval such that an opening of the aortic valve may be evidenced based on a detected signal curve and/or a hemodynamic variable or an operating parameter of the blood pump.

10. A blood pump for supporting a heart, the blood pump comprising:
    a rotor with delivery elements;
    a rotor drive;
    a pressure sensor;
    a regulating device configured to regulate a pressure by control of the rotor drive, wherein the regulating device is configured to regulate a specific pressure parameter successively to different target values; and
    wherein the regulating device is configured to regulate to varying target values during operation of the rotor drive such that at least one prespecified feature of a temporal curve of the pressure, a flow, a motor current, or a bearing position is attained.

11. The blood pump according to claim 10, wherein the pressure sensor, or a flow sensor is connected directly to the regulating device.

12. The blood pump according to claim 10, wherein the pressure sensor comprises two pressure sensors, of which a first is arranged in or on the blood pump and a second is arranged in a volume not connected directly to the blood pump.

13. The blood pump according to claim 10, wherein the pressure sensor is configured to determine the pressure parameter, and/or the regulating device is configured to determine the pressure parameter from operating parameters of the blood pump.

14. The blood pump according to claim 10, wherein the regulating device is embodied such that the pressure parameter is determined by one or a plurality of operating parameters of the blood pump.

15. The blood pump according to claim 10, wherein the pressure parameter is a hemodynamic pressure parameter.

16. The blood pump according to claim 10, wherein the regulating device is configured to use an end-diastolic pressure determined from a cyclic pressure curve in the detection range of the pressure sensor.

17. The blood pump according to claim 10, wherein the regulating device is suitable for periodically regulating to different target values.

18. The blood pump according to claim 10, wherein the regulating device is configured to regulate the rotor drive alternating periodically such that an opening of the aortic valve may be evidenced based on a detected signal curve or an operating parameter of the blood pump.

19. The blood pump according to claim 10, wherein the regulating device has a first operating state that corresponds to a first operation of the blood pump and a second operating state that is configured to regulate the rotor drive for a time interval such that an opening of the aortic valve may be evidenced based on a detected signal curve or an operating parameter of the blood pump.

* * * * *